US011819570B2

(12) United States Patent
Suganami et al.

(10) Patent No.: US 11,819,570 B2
(45) Date of Patent: Nov. 21, 2023

(54) TEMPERATURE-RESISTANT SUGAR-RESPONSIVE GEL

(71) Applicants: National University Corporation Tokai National Higher Education and Research System, Nagoya (JP); National University Corporation Tokyo Medical and Dental University, Tokyo (JP)

(72) Inventors: Takayoshi Suganami, Nagoya (JP); Miyako Tanaka, Nagoya (JP); Akira Matsumoto, Tokyo (JP); Hiroko Matsumoto, Tokyo (JP); Yuki Morooka, Tokyo (JP); Yuji Miyahara, Tokyo (JP)

(73) Assignees: National University Corporation Tokai National Higher Education and Research System, Nagoya (JP); National University Corporation Tokyo Medical and Dental University, Tokyo (JP)

( * ) Notice: Subject to any disclaimer, the term of this patent is extended or adjusted under 35 U.S.C. 154(b) by 0 days.

(21) Appl. No.: 17/055,032

(22) PCT Filed: May 31, 2019

(86) PCT No.: PCT/JP2019/021766
§ 371 (c)(1),
(2) Date: Nov. 12, 2020

(87) PCT Pub. No.: WO2019/230961
PCT Pub. Date: Dec. 5, 2019

(65) Prior Publication Data
US 2021/0121400 A1    Apr. 29, 2021

(30) Foreign Application Priority Data

Jun. 1, 2018  (JP) ................................ 2018-105788

(51) Int. Cl.
| | |
|---|---|
| *A61K 9/06* | (2006.01) |
| *A61K 38/28* | (2006.01) |
| *A61K 47/32* | (2006.01) |
| *A61M 37/00* | (2006.01) |

(52) U.S. Cl.
CPC ................ *A61K 9/06* (2013.01); *A61K 38/28* (2013.01); *A61K 47/32* (2013.01); *A61M 37/0015* (2013.01); *A61M 2037/0023* (2013.01)

(58) Field of Classification Search
CPC .......... A61K 9/06; A61K 38/28; A61K 47/32; A61K 9/0024; A61K 47/18; A61K 47/24; A61M 37/0015; A61M 2037/0023; C08F 220/54; A61P 3/10
See application file for complete search history.

(56) References Cited

U.S. PATENT DOCUMENTS

| | | | |
|---|---|---|---|
| 2012/0283403 A1* | 11/2012 | Matsumoto | ........... C08F 220/56 562/7 |
| 2013/0066264 A1 | 3/2013 | Matsumoto et al. | |
| 2015/0226728 A1 | 8/2015 | Yoshioka et al. | |
| 2018/0333495 A1 | 11/2018 | Matsumoto et al. | |

FOREIGN PATENT DOCUMENTS

| | | |
|---|---|---|
| EP | 2 522 679 A1 | 11/2012 |
| EP | 2 578 234 A1 | 4/2013 |
| JP | H 1995-126323 A | 5/1995 |
| JP | 2011-140537 A | 7/2011 |
| JP | 2015-110623 A | 6/2015 |
| JP | 2015-151427 A | 8/2015 |
| JP | 2016-209372 A | 12/2016 |
| WO | WO 2017/069282 A1 | 4/2017 |

OTHER PUBLICATIONS

Matsumoto et al. (WO2017069282A1 Machine Translation) (Year: 2017).*
Liu, Lei et al., "A Versatile Dynamic Mussel-Inspired Biointerface: From Specific Cell Behavior Modulation to Selective Cell Isolation", Angew. Che,. Int. Ed., May 25, 2018, vol. 57, pp. 7878-7882.
Li, Siqi et al., "Synthesis and Development of Poly(N-Hydroxyethyl Acrylamide)-Ran-3-Acrylamidophenylboronic Acid Polymer Fluid for Potential Application in Affinity Sensing of Glucose", Journal of Diabetes Science and Technology, Sep. 2011, vol. 5, Issue 5,2011, pp. 1060-1067.
International Search Report in International Application No. PCT/JP2019/021766 dated Aug. 6, 2019.
International Preliminary Report on Patentability in International Application No. PCT/JP2019/021766 dated Dec. 17, 2020.
Extended European Search Report in European Patent Application No. 19810343.4, dated Feb. 23, 2022.

* cited by examiner

*Primary Examiner* — Robert A Wax
*Assistant Examiner* — Quanglong N Truong
(74) *Attorney, Agent, or Firm* — Knobbe, Martens, Olson & Bear, LLP

(57) ABSTRACT

A sugar-responsive gel that is highly resistant to temperature changes, and a sugar-responsive drug delivery device including such a gel. The sugar-responsive gel, which comprises a gel composition including a monomer having a hydroxyl group in addition to a phenylboronic-acid-based monomer, can exhibit suitable temperature resistance. A sugar-responsive drug delivery device including such a sugar-responsive gel is less susceptible to the effects of temperature changes, and therefore can prevent undesirable excessive delivery of a drug such as insulin.

10 Claims, 6 Drawing Sheets

TEMPERATURE-RESISTANT SUGAR-RESPONSIVE GEL

CROSS-REFERENCE TO RELATED APPLICATIONS

The present application is an application claiming the benefit of priority to JP 2018-105788 (filing date: Jun. 1, 2018), which is incorporated herein by reference in its entirety.

TECHNICAL FIELD

The present invention relates to glucose-responsive gels and a drug delivery device using the gel. More specifically, the present invention relates to temperature-resistant glucose-responsive gels and a drug-administering device responsive to blood sugar concentration using the gel, particularly an insulin-administering device (artificial pancreas device).

BACKGROUND ART

The glucose concentration in blood (blood glucose level) is adjusted within a certain range by the action of various hormones such as insulin, but when this regulatory function is disrupted, the sugar content in blood increases abnormally resulting in diabetes. Treatment of diabetes usually involves measuring the blood glucose level and injecting insulin. However, overdose of insulin can cause brain damage. Therefore, in diabetic treatment, it is important to adjust the amount of insulin delivered according to the blood glucose concentration.

Meanwhile, phenylboronic acid (PBA) which is capable of reversibly binding to glucose is very effective for detection of glucose and delivery of self-regulatory insulin, and such properties of the phenylboronic acid are being utilized for development of insulin delivery devices. For example, Patent Document 1 (Japanese Unexamined Patent Publication No. 2015-110623) discloses a glucose-responsive gel as well as an insulin-administering device, in which under the physiological conditions of pKa 7.4 or less and temperature 35° C. to 40° C., when the glucose concentration increases, insulin can be released from the gel itself accordingly; and insulin released from the gel itself can be suppressed when the glucose concentration decreases. Further, Patent Document 2 (Japanese Unexamined Patent Publication No. 2016-209372) discloses an insulin delivery device having a gel-filling unit in which a co-polymer gel composition containing a phenylboronic acid-based monomer as a monomer is present, an insulin solution-filling unit surrounding the gel-filling unit, and a catheter or needle having an opening for insulin release to accommodate the gel-filling unit. Patent Document 3 also discloses a device capable of releasing a drug depending on stimuli such as glucose concentration, which is improved by using a porous body such as a hollow fiber having biocompatibility and drug permeability.

For example, according to the insulin delivery device disclosed in Patent Document 2, a gel filling unit is inserted subcutaneously or intradermally as being contained within a catheter or needle. When the glucose concentration in blood is higher in this state, the gel composition of the gel-filled unit is swelled upon binding of glucose, and insulin diffused in the gel-filled unit is released into the blood through an opening in the catheter or needle. When the glucose concentration is low, the gel composition contracts and insulin release is suppressed. This makes it possible to deliver insulin according to the glucose concentration.

CITATION LIST

Patent Documents

Patent Document 1: Japanese Patent Application Kokai Publication No. (JP-A) 2015-110623 (unexamined, published Japanese patent application)

Patent Document 2: Japanese Patent Application Kokai Publication No. (JP-A) 2016-209372 (unexamined, published Japanese patent application)

Patent Document 3: International publication pamphlet WO2017/069282

SUMMARY OF THE INVENTION

Problems to be Solved by the Invention

Normally, the body temperature of mammals including humans is kept substantially constant, but for example, when starting treatment with a drug delivery device, the patient's body temperature may drop temporarily after anesthetizing the patient or immediately after mounting the drug delivery device to the body. At that time, it is not desirable that the drug delivery becomes excessive when the gel in the drug delivery device is affected by the temperature change. For example, excessive delivery of insulin causes hypoglycemia. Therefore, one of the objectives of the present invention is to provide a glucose-responsive gel having high resistance to temperature changes. Another objective of the present invention is to provide a drug delivery device using a gel having resistance to such temperature changes.

Means for Solving the Problems

The present inventors have found that that a gel having resistance to temperature change can be produced by adding a monomer having a hydroxyl group such as HEAAm as a new component to a conventional glucose-responsive gel composition. The present invention is based on such findings and encompasses, for example, the embodiments below.

Embodiment 1

A glucose-responsive gel consisting of a gel composition comprising a phenylboronic acid-based monomer represented by the general formula (1) below:

[Chemical Structure 1]

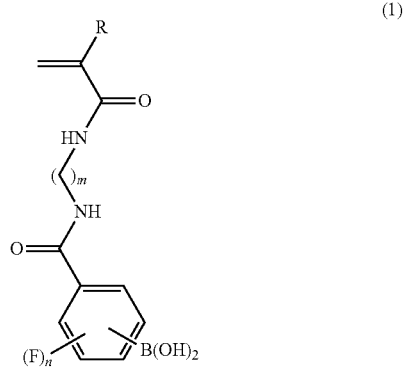

(1)

wherein R is H or CH$_3$, F is present independently, n is either 1, 2, 3 or 4, m is 0 or an integer greater equal to 1 or more, and
a monomer represented by general formula (2) below:

[Chemical Structure 2]

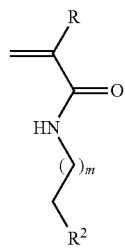

(2)

wherein R$^1$ is H or CH$_3$, m is 0 or an integer equal to 1 or more, and R$^2$ is OH, a saturated or unsaturated C$_{1-6}$ alkyl group substituted with one or more hydroxyl groups, a saturated or unsaturated C$_{3-10}$ cycloalkyl group substituted with one or more hydroxyl groups, a C$_{3-12}$ heterocyclic group containing 1 to 4 heteroatoms selected from NH, O and S substituted with one or more hydroxyl groups, a C$_{6-12}$ aryl group substituted with one or more hydroxyl groups, a monosaccharide group, or a polysaccharide group.

Embodiment 2

The glucose-responsive gel according to embodiment 1, wherein the phenylboronic acid-based monomer represented by the general formula (1) is 4-(2-acrylamidoethylcarbamoyl)-3-fluorophenylboronic acid (AmECFPBA).

Embodiment 3

The glucose-responsive gel according to embodiment 1 or 2, wherein the monomer represented by the general formula (2) is N-hydroxyethylacrylamide (HEAAm).

Embodiment 4

The glucose-responsive gel according to any one of embodiments 1 to 3, further comprising N-isopropylmethacrylamide (NIPMAAm) in the gel composition.

Embodiment 5

The glucose-responsive gel according to any one of embodiments 1 to 4, further comprising a cross-linking agent in the gel composition.

Embodiment 6

The glucose-responsive gel according to embodiment 5, wherein the crosslinking agent is N,N'-methylenebis-(acrylamide) (MBAAm).

Embodiment 7

The glucose-responsive gel according to any one of embodiments 1 to 6, wherein the gel composition comprises 1 mol % to 40 mol % of a phenylboronic acid-based monomer represented by the general formula (1).

Embodiment 8

The glucose-responsive gel according to any one of embodiments 1 to 7, wherein the gel composition comprises 1 mol % to 40 mol % of the monomer represented by the general formula (2).

Embodiment 9

The glucose-responsive gel according to any one of embodiments 1 to 8, wherein the gel composition comprises 20 mol % to 80 mol % of N-isopropyl methacrylamide (NIPMAAm).

Embodiment 10

The glucose-responsive gel according to any one of embodiments 1 to 9, wherein the gel composition comprises about 30 mol % of the phenylboronic acid-based monomer represented by the general formula (1), about 30 mol % of the monomer represented by the general formula (2), and about 40 mol % of N-isopropylmethacrylamide (NIPMAAm).

Embodiment 11

A drug delivery device comprising the glucose-responsive gel according to any one of embodiments 1 to 10.

Embodiment 12

The drug delivery device according to embodiment 11, which is an implantable-type or microneedle-type device.

Embodiment 13

The drug delivery device according to embodiment 11 or 12, which is a device for use in insulin delivery.

Embodiment 14

A glucose-responsive gel consisting of a gel composition comprising 25 mol % to 35 mol % of a phenylboronic acid-based monomer represented by the general formula (1) below:

[Chemical Structure 3]

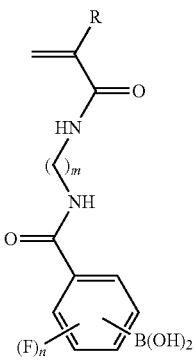

(1)

wherein R is H or CH$_3$, F is present independently, n is either 1, 2, 3 or 4, m is 0 or an integer equal to 1 or more, 25 mol % to 35 mol % of a monomer represented by the general formula (2) below:

[Chemical Structure 4]

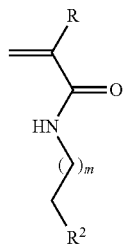
(2)

wherein $R^1$ is H or $CH_3$, m is 0 or an integer of 1 or more, and $R^2$ is OH, a saturated or unsaturated $C_{1-6}$ alkyl group substituted with one or more hydroxyl groups, a saturated or unsaturated $C_{3-10}$ cycloalkyl group substituted with one or more hydroxyl groups, a $C_{3-12}$ heterocyclic group containing 1 to 4 heteroatoms selected from NH, O and S substituted with one or more hydroxyl groups, a $C_{6-12}$ aryl group substituted with one or more hydroxyl groups, a monosaccharide group, or a polysaccharide group], and
30 mol % to 50 mol % of N-isopropylmethacrylamide (NIPMAAm).

Effect of the Invention

According to the present invention, it is possible to provide glucose-responsive gels showing excellent temperature resistance, and a drug delivery device using such gels. Since such glucose-responsive gels are less susceptible to temperature changes, they can prevent unwanted excessive delivery of drugs (such as insulin) even when the body temperature of the patient wearing the device drops for some reason.

MODE FOR CARRYING OUT THE INVENTION

Figure 1:
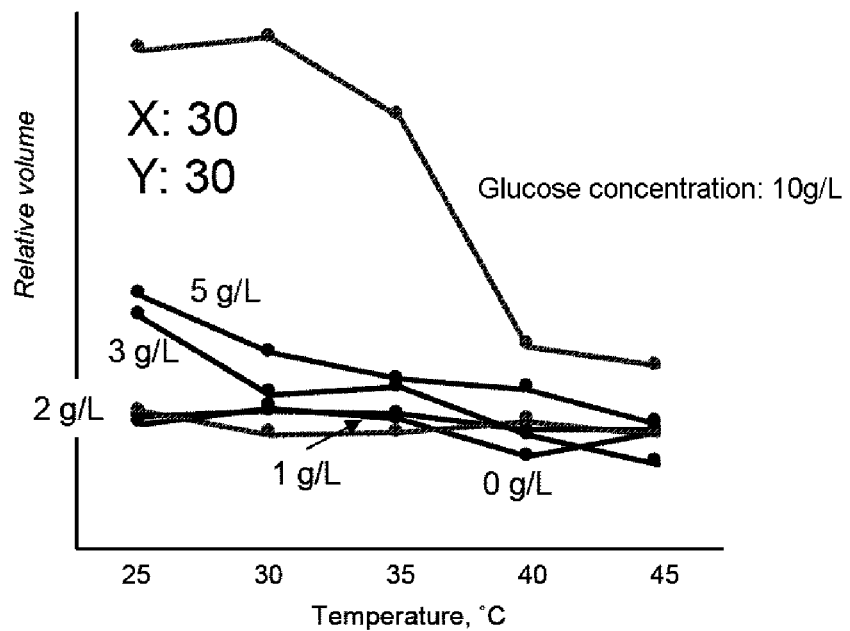
FIG. 1 is a graph showing the result of preparing a gel by mixing N-isopropylmethacrylate (NIPMAam) as a gelling agent (main chain) and 4-(2-acrylamidoethylcarbamoyl)-3-fluorophenylboronic acid (AmECFPBA) as a phenylboronic acid-based monomer, N-hydroxyethylacrylamide (HEAAm) as a hydroxylic monomer, N,N'-methylenebis-(acrylamide) (MBAAm) as a crosslinking agent, 2,2'-Azobisisobutyronitrile as a polymerization initiator at a charged molar ratio of 62/27/11/5/0.1, and carrying out radical polymerization; and investigating the glucose responsiveness of the obtained gel in the temperature range of 25° C. to 45° C. The horizontal axis is temperature (Temperature), and the vertical axis is relative volume of the gels (Relative volume). The test was performed for each glucose concentration of 0 g/L, 1 g/L, 2 g/L, 3 g/L, 5 g/L and 10 g/L. It was found that the gel containing HEAAm can significantly reduce the temperature dependence near the normal glycemic level (1 g/L).

The present invention will be described in detail below.

A glucose-responsive gel comprising a gel composition containing a phenylboronic acid-based monomer represented by the general formula (1) below:

[Chemical Structure 5]

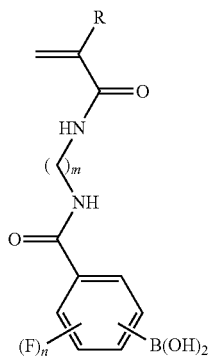

(1)

[In the formula, R is H or $CH_3$, F is present independently, n is either 1, 2, 3 or 4, m is an integer greater than or equal to 0 or 1.], and a monomer (hereinafter, also referred to as a hydroxyl-based monomer) represented by the general formula (2) below:

[Chemical Structure 6]

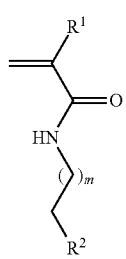

(2)

[In the formula, $R^1$ is H or $CH_3$, m is an integer of 0 or 1 or more, and $R^2$ is OH, a saturated or unsaturated $C_{1-6}$ alkyl group substituted with one or more hydroxyl groups, a saturated or unsaturated $C_{3-10}$ cycloalkyl group substituted with one or more hydroxyl groups, a $C_{3-12}$ heterocyclic group containing 1 to 4 heteroatoms selected from NH, O and S substituted with one or more hydroxyl groups, a $C_{6-12}$ aryl group substituted with one or more hydroxyl groups, a monosaccharide group, or a polysaccharide group.] In other words, the glucose-responsive gel of the present invention comprises a co-polymer containing a phenylboronic acid-based monomer unit represented by the above general formula (1) and a monomer unit represented by the above formula (2). The term "monomer unit" as used herein means a structural unit of a (co)-polymer derived from monomers.

<Gel composition> The present invention, as described below, utilizes a mechanism which changes the structure of phenylboronic acid monomers depending on the glucose concentration.

[Chemical Structure 7]

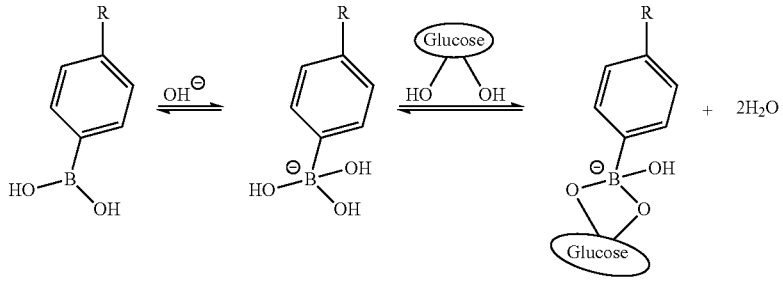

Phenylboronic acid (PBA) which dissociates in water binds reversibly to a sugar molecule, maintaining the equilibrium state described above. When the glucose concentration is high, glucose binds to boronic acid and the volume of the gel swells, but when the glucose concentration is low, it contracts. When the drug delivery device is filled with the gel, this reaction occurs at the gel interface in contact with blood, and the gel shrinks only at the interface to form a dehydrated shrinking layer, which we call the "skin layer". The insulin delivery device according to an embodiment of the present invention takes advantage of this property for controlled release of insulin.

The phenylboronic acid-based monomer used for preparing the gel composition according to the present invention is represented by the general formula (1) below:

[Chemical Structure 8]

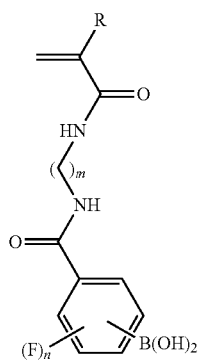

(1)

[In the formula, R is H or CH$_3$, F exists independently, n is either 1, 2, 3 or 4, and m is an integer of 0 or 1 or more.]

The above-mentioned phenylboronic acid monomer has a fluorinated phenylboronic acid in which hydrogen on the phenyl ring is substituted with one to four fluorines, and a structure in which the phenyl ring is bound by the carbon of the amide group. The phenylboronic acid-based monomer having the above structure has high hydrophilicity, and the phenyl ring is fluorinated, so that pKa can be set to the biological level of 7.4 or less. Furthermore, this phenylboronic acid-based monomer not only acquires sugar recognition ability in a biological environment, but also enables co-polymerization with a gelling agent and a cross-linking agent described later by unsaturated bonds, thereby enabling the formation of a gel that undergoes a phase change depending on the glucose concentration.

In the above phenylboronic acid-based monomer, when one hydrogen on the phenyl ring is substituted with fluorine, the location at which F and B(OH)$_2$ are introduced may be any of ortho, meta, and para.

Generally, it is possible to lower the pKa with a phenylboronic acid-based monomer when m is set to 1, as compared to a phenylboronic acid-based monomer when m is set to 0. The upper limit of m is not particularly limited, but it is, for example, 20 or less, preferably 10 or less, and more preferably 4 or less.

As an example of the above-mentioned phenylboronic acid-based monomer, there is a phenylboronic acid-based monomer in which R is hydrogen, n is 1 and m is 2; and a particularly preferred phenylboronic acid-based monomer is 4-(2-acrylamido-ethylcarbamoyl)-3-fluorophenylboronic acid (4-(2-acrylamidoethylcarbamoyl)-3-fluorophenylboronic acid, (AmECFPBA)).

The phenylboronic acid-based monomer represented by the general formula (1) is contained in the gel composition, for example, at 1 mol % or more, 5 mol % or more, 10 mol % or more, 15 mol % or more, 20 mol % or more, 25 mol % or more, 30 mol % or more, 35 mol % or more, 40 mol % or more, 45 mol % or more, 50 mol % or more, or 60 mol % or more. Further, the phenylboronic acid-based monomer represented by the general formula (1) is contained in the gel composition, for example, at 90 mol % or less, 80 mol % or less, 70 mol % or less, 60 mol % or less, 50 mol % or less, 45 mol % or less, 40 mol % or less, 35 mol % or less, 30 mol % or less, 25 mol % or less, or 20 mol % or less. The concentration range of the phenylboronic acid-based monomer represented by the general formula (1) contained in the gel composition is, for example, a percentage range of 10 mol % to 90 mol %, 15 mol % to 45 mol %, or 25 mol % to 35 mol %. The concentration range can be specified by any combination of the above upper and lower limits. The preferable ratio of the phenylboronic acid-based monomer is about 30 mol %. In addition, in this specification, the term "about" is used to refer to a range of 10% before and after the numerical value following it. That is, about 30 mol % means a range of 27 mol % to 33 mol %.

The gel composition according to the present invention comprises, in addition to the above-mentioned phenylboronic acid-based monomer, a monomer (hydroxyl monomer) represented by the general formula (2) below:

[Chemical Structure 9]

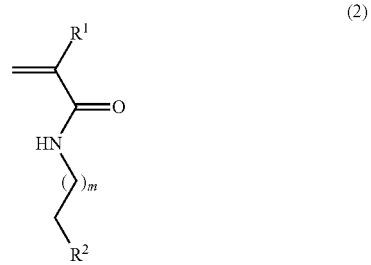

(2)

[In the formula, R$^1$ is H or CH$_3$, m is an integer of 0 or 1 or more, and R$^2$ is OH, a saturated or unsaturated C$_{1-6}$ alkyl group substituted with one or more hydroxyl groups, a saturated or unsaturated C$_{3-10}$ cycloalkyl group substituted with one or more hydroxyl groups, a C$_{3-12}$ heterocyclic group containing 1 to 4 heteroatoms selected from NH, O and S substituted with one or more hydroxyl groups, a C$_{6-12}$ aryl group substituted with one or more hydroxyl groups, a monosaccharide group, or a polysaccharide group.]

The monomer of the general formula (2) has a hydroxyl group in the molecule. Without being bound by any particular theory, this hydroxyl group increases the hydrophilicity of the gel, offsetting the hydrophobicity of the gel and works on the boronic acid in the gel to have an effect of preventing excessive swelling of the gel. The upper limit of m is not particularly limited, and is, for example, 20 or less, preferably 10 or less, and more preferably 4 or less.

An example of the above-mentioned hydroxyl monomer is a monomer in which R$^1$ is hydrogen, m is 1, and R$^2$ is OH, and the particularly preferred hydroxyl monomer is N-(Hydroxyethyl) acrylamide (N-(Hydroxyethyl) acrylamide, HEAAm). In particular, by using ethyl instead of methyl for the side chain, there is an effect of increasing the degree of freedom of rotation of the side chain and remarkably improving the efficiency of the intermolecular (boronic acid side chain) cross-linking reaction. Therefore, the most optimal gel that undergoes phase changes depending on the glucose concentration may be generated by making the monomer HEAAm. In the examples of other hydroxyl monomers, R$_2$ may be, for example, a sugar derivative such as a catechol group or a glycolyl group. The monosaccharide can be, for example, glucose.

The hydroxyl monomer represented by the general formula (2) is contained in the gel composition, for example, at 1 mol % or more, 5 mol % or more, 10 mol % or more, 15 mol % or more, 20 mol % or more, 25 mol % or more, 30 mol % or more, 35 mol % or more, 40 mol % or more, 45 mol % or more, 50 mol % or more, or 60 mol % or more. Further, the hydroxyl monomer represented by the general formula (2) is contained in the gel composition, for example, at 90 mol % or less, 80 mol % or less, 70 mol % or less, 60 mol % or less, 50 mol % or less, 45 mol % or less, 40 mol % or less, 35 mol % or less, 30 mol % or less, 25 mol % or less, or 20 mol % or less. The concentration range of the hydroxyl monomer represented by the general formula (2) in the gel composition is, for example, a percentage range of 10 mol % to 90 mol %, 15 mol % to 45 mol %, 20 mol % to 40 mol %, or 25 mol % to 35 mol %. The concentration range can be specified by any combination of the above upper and lower limits. The preferred ratio of the hydroxyl monomer is about 10 mol %. In addition, in this specification, the term "about" is used to refer to a range of 10% before and after the numerical value following it. That is, about 30 mol % means a range of 27 mol % to 33 mol %.

The gel composition can be prepared from a gelling agent having the property of not inducing any toxic effect or adverse effect on the biological functions in the body (biocompatibility), the phenylboronic acid-based monomer described above, the hydroxyl monomer described above, and a cross-linking agent. The method for preparing the gel is not particularly limited, but first, a gelling agent serving as the main chain of the gel, a phenylboronic acid-based monomer, a hydroxyl monomer, and a cross-linking agent are mixed at a predetermined charged molar ratio to allow a polymerization reaction. For polymerization, a polymerization initiator is used as needed.

As the polymerization initiator, an initiator known to those skilled in the art, for example, 2,2'-azobisisobutyronitrile (AIBN), or 1,1'-azobis(cyclohexanecarbonitrile) (ABCN) can be used. The percentage of the polymerization initiator added to the gel composition can be, for example, about 0.1 mol %.

The polymerization reaction can be carried out, for example, using dimethyl sulfoxide (DMSO) as a reaction solvent; and the reaction temperature can be, for example, 60° C., and the reaction time can be, for example, 24 hours. However, these conditions can be appropriately adjusted by those skilled in the art.

In one embodiment of the present invention, it is preferable that the gel composition of the drug delivery device contains a drug (for example, insulin) in advance. For that purpose, the drug can be diffused into the gel by immersing the gel in an aqueous solution such as a phosphate buffered aqueous solution containing the drug at a predetermined concentration. Next, the gel taken out from the aqueous solution is immersed in hydrochloric acid, for example, for a predetermined time to form a thin dehydrated shrinking layer (referred to as a skin layer) on the surface of the gel body, thereby encapsulating (loading) the drug and obtaining a gel that can be filled into a device.

The preferred ratio of the gelling agent, a phenylboronic acid-based monomer, a hydroxyl monomer, and a crosslinking agent enables release of insulin in response to glucose concentration under physiological conditions, and it can be varied depending on the monomer or such used, without particular limitations. Any composition may be used as long as it exhibits a desired temperature resistance. The present inventors have previously prepared gels by combining different phenylboronic acid-based monomers in various ratios with gelling agents and cross-linking agents, and have investigated their behavior (for example, refer to Japanese Patent No. 5622188). A person skilled in the art can obtain a gel having a suitable composition based on the description in the present specification and the technical information reported in the field of the art. Methods for preparing and analyzing glucose-responsive gels containing a phenylboronic acid-based monomer unit include, for example, Matsumoto et al., Angew. Chem. Int. Ed. 2012, 51, 2124-2128, and Matsumoto et., Sci. Adv. 2017; Vol. 3, no. 11, eaaq0723.

Suitable applicable gel compositions in the present invention can be prepared by, for example, mixing N-isopropyl methacrylamide (NIPMAAm) as a gelling agent (main chain), 4-(2-acrylamide ethylcarbamoyl)-3-fluorophenylboronic acid (AmECFPBA) as a phenylboronic acid-based monomer, N-hydroxyethyl acrylamide (HEAAm) as a hydroxyl monomer, N,N'-methylenebis-(acrylamide) (MBAAm) as a crosslinking agent, 2,2'-azobisisobutyronitrile as a polymerization initiator, at a charged molar ratio of 62/27/11/5/0.1. By adjusting in this way, the temperature dependence in the vicinity of the normal blood glucose level (1 g/L) can be significantly reduced, as shown in FIG. 1. However, the present invention is not limited thereto. If a gel body formed by a gel composition containing a gelling agent, a phenylboronic acid-based monomer, a hydroxyl monomer and a crosslinking agent can swell or contract in response to glucose concentration, as well as show the desired temperature resistance, a gel may be prepared by setting the charged molar ratio of the gelling agent/phenylboronic acid-based monomer/hydroxyl monomer/crosslinking agent to other various values.

The gelling agent may be any biocompatible material that is biocompatible and can be gelled, and is a biocompatible acrylamide compound (a compound having one acrylamide group or a methacrylamide group), for example. Specific examples are N-isopropylmethacrylamide (NIPMAAm), N-isopropylacrylamide (NIPAAm), N,N-dimethylacrylamide (DMAAm), N,N-diethylacrylamide (DEAAm), and such.

The gelling agent can be contained in a gel composition at a ratio of, for example, 20 mol % or more, 25 mol % or more, 30 mol % or more, 35 mol % or more, 40 mol % or more, 45 mol % or more, 50 mol % or more, 60 mol % or more, 70 mol % or more, or 80 mol % or more. Further, the gelling agent can be contained in a gel composition at a ratio of, for example, 90 mol % or less, 80 mol % or less, 70 mol % or less, 60 mol % or less, 50 mol % or less, 45 mol % or less, 40 mol % or less, 35 mol % or less, 30 mol % or less, 25 mol % or less, or 20 mol % or less. The concentration range of the gelling agent contained in the gel composition may be a percentage range of, for example, 10 mol % to 90 mol %, 15 mol % to 75 mol %, 20 mol % to 60 mol %, 25 mol % to 55 mol %, or 35 mol % to 45 mol %. The concentration range can be specified by any combination of the above upper and lower limits. The preferred gelling agent ratio is about 60 mol %.

The crosslinking agent may be any substance that has biocompatibility and can crosslink monomers, and is preferably a compound having at least two acrylamide groups or methacrylamide groups in the molecule, for example, N,N'-methylenebis-(acrylamide) (MBAAm), ethylene glycol dimethacrylate (EGDMA), N,N'-methylenebisacrylamide (MBMAAm), and other various crosslinking agents.

The crosslinking agent can be contained in the gel composition, for example, at 0.1 mol % or more, 0.3 mol % or more, 0.5 mol % or more, 1 mol % or more, 2 mol % or more, 3 mol % or more, 4 mol % or more, or 5 mol % or more. Further, the cross-linking agent can be contained in the gel composition at a ratio of, for example, 10 mol % or less, 5 mol % or less, 3 mol % or less, 2 mol % or less, 1.5 mol % or less, 1 mol % or less, or 0.5 mol % or less. The concentration range of the cross-linking agent contained in the gel composition may be a percentage range of, for example, 0.1 mol % to 10 mol %, 0.3 mol % to 2 mol %, or 0.5 mol % to 1.5 mol %. The concentration range can be specified by any combination of the above upper and lower limits. The preferred ratio of the cross-linking agent is about 1 mol %.

Thus, in a preferred embodiment of the present invention, the gel composition is prepared by polymerizing N-isopropylmethacrylamide (NIPMAAm), 4-(2-acrylamidoethylcarbamoyl)-3-fluorophenylboronic acid (AmECFPBA), N-hydroxyethylacrylamide (HEAAm), N,N'-methylenebis(acrylamide) (MBAAm) at a charged molar ratio of 62/27/11/5 (mol %) as shown below.

In the above gel composition, a phenylboronic acid-based monomer and a hydroxyl monomer co-polymerize with a gelling agent and a crosslinking agent to form a gel body. A drug such as insulin can be diffused into this gel, and the surface of the gel body can be surrounded by a dehydrated shrinking layer. As a result, under physiological conditions (for example, pKa 7.4 or less, temperature 35° C. to 40° C.), when the glucose concentration becomes high, the dehydrated shrinking layer disappears due to swelling, and the drug (for example, insulin) in the gel is released to the outside. On the other hand, when the glucose concentration becomes low again, the swelled gel contracts and a dehydrated shrinking layer (skin layer) is formed again on the entire surface, and release of the drug (for example, insulin) in the gel to the outside is suppressed. Therefore, the gel composition used in the present invention can autonomously release a drug (for example, insulin) in response to glucose concentration.

<Drug>

The drug that can be delivered using a gel of the present invention can be a protein, peptide, nucleic acid, a different high molecular polymer, a low molecular compound, without being limited thereto. The drug may be a therapeutic agent for a disease, a prophylactic drug, a vaccine, a nutritional supplement, or such. A particularly preferred drug is insulin. A variety of naturally occurring insulin or modified insulin have become available by synthesis or purchase of commercially available products. As insulin, for example, Humarin (registered trademark) may be used. Humarin (registered trademark) is a human (genetic recombination) insulin marketed by Eli Lilly and Co. Various insulin preparations including the fast-acting type, intermediate type, and long-acting type have been developed, and they can be appropriately selected and used.

In the drug delivery device according to the present invention, the drug may be contained in the gel composition in advance. For this purpose, by immersing the gel in an aqueous solution that contains a predetermined concentration of the drug (e.g., phosphate-buffered aqueous solution), it is possible to allow the drug to diffuse into the gel. Next, the gel taken out from the aqueous solution is immersed in hydrochloric acid, for example, for a predetermined time to form a thin dehydrated shrinking layer (referred to as a skin layer) on the surface of the gel body, thereby encapsulating (loading) the drug and obtaining a gel that can be filled into the device.

<Device>

The drug delivery device according to the present invention contains the above-described glucose-responsive gel, and is preferably used in the delivery of insulin. The drug delivery device according to the present invention may take any form, including an implantable type and a microneedle type. For the device to be implanted in the body, for example, one can refer to Japanese Patent Application Kokai Publication No. (JP-A) 2016-209372 (unexamined, published Japanese patent application) and International Publication Pamphlet WO2017/069282.

Figure 5A:
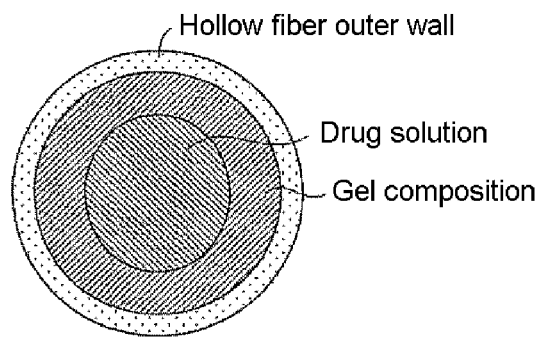
FIG. 5A schematically shows an example of a cross-sectional view of a drug delivery device according to the present invention, which is an example of a hollow fiber structure having a gel filled inside the hollow fiber and a drug solution filled inside the gel.

In one embodiment of the invention, the drug delivery device may take the form of an implantable hollow fiber fusion device. Hereinafter, the configuration of the insulin delivery device according to one embodiment will be described more specifically with reference to the drawings. FIG. 5A schematically shows an example of a cross-sectional view of the device of the present invention using a porous body. In this device, a hollow fiber is used as a porous body, a gel composition is filled along the inner wall of the hollow fiber, and a drug solution is filled inside the gel composition. The gel may also be present in the pores of the outer wall of the hollow fiber, depending on the method of manufacturing the device and its usable form in the body. Further, in this figure, there is a section filled with the drug solution inside the gel composition, but a structure without such a section is also possible, in which the gel composition containing the drug is uniformly filled inside the hollow fiber structure.

The device of the present invention can be constituted from a single hollow fiber structure of the aforementioned structure, or by using the hollow fiber structure in the range of 2 to 100,000, without being limited thereto. The device of the present invention may also be provided with a reservoir so that the drug can be replenished after the drug is released from the porous body (hollow fiber) or the drug release body (drug release unit). The reservoir for the hollow fiber may be in the form of a catheter having an outer diameter of 1 mm to 2 mm and a length of 10 mm to 200 mm, and a commercially available silicon catheter of 4 French size (inner diameter: 0.6 mm/outer diameter: 1.2 mm) can be preferably used. In the case where a reservoir is created, for example, a drug solution of about 10 ml to 30 ml is packed for replenishment, and through the opening connected to the open end or drug release unit of the hollow fiber structure, it is possible to allow continuous controlled release of the drug during the desired period of insertion or wearing. It is not always necessary to provide a reservoir as long as it is possible to maintain the quantity of the drug required to be delivered for a predetermined period of time.

Figure 5B:
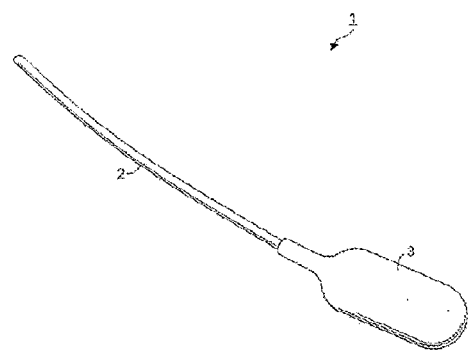
FIG. 5B schematically shows another example of the structure of the drug delivery device according to the present invention. Device 1 has catheter 2 and reservoir 3, and catheter 2 is provided with a side hole.
Figure 5C:
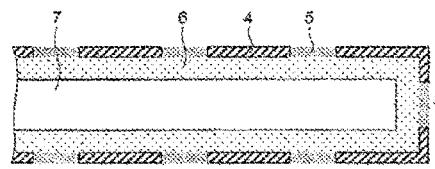
FIG. 5C shows an enlarged view of the catheter in FIG. 5B. Catheter side wall 4 is provided with a plurality of side holes 5. Gel filling unit 6 is provided along the inside of the inner wall of the catheter, and drug-filling unit 7 is set up in the hollow unit which has not been filled with the gel.

FIG. 5B shows an example of the appearance of a device which is another embodiment of the present invention. In this embodiment, device 1 has catheter 2 as a drug releaser and reservoir 3. Catheter 2 has, for example, a tube shape with an outer diameter of 1 mm to 2 mm and a length of 10 mm to 200 mm, and a commercially available silicon catheter of 4 French size can be preferably used. As shown in FIG. 5C, the catheter has a plurality of side holes 5 as a drug release unit on side wall 4. The side hole can also be provided at the tip of the catheter, regardless of its name. Along the inner wall of the catheter, a gel-filled unit 6 is filled in which a co-polymer gel composition containing a phenylboronic acid-based monomer as a monomer is present, and a drug filling unit 7 is provided so as to have the drug solidified in the gel-filled unit 6. One of the features of the device of the present embodiment is that the drug filling unit 7 exists in a section surrounded by the gel filling unit 6, and it is possible to fill a section closer to the drug releasing unit with a high-concentration drug. By setting the thickness of the gel filling unit 6 within the range of 10 to 500 μm in the catheter, it is possible to control release of the drug (insulin) depending on the glucose concentration. The reservoir 3 is provided so that the drug filling unit 7 can be replenished with the drug, and the drug filling unit in the catheter and the reservoir are filled with, for example, up to about 10 ml of the drug, and continuous controlled release of the drug can be allowed during the desired insertion or wearing period.

Figure 5D:
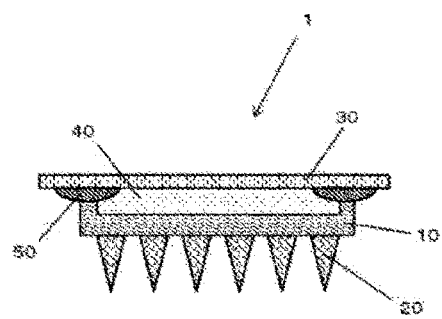
FIG. 5D shows a schematic cross-sectional view of the insulin delivery microneedle which is an embodiment of a drug delivery device of the present invention.

FIG. 5D shows an example of the appearance of a device which is yet another embodiment of the present invention. With reference to FIG. 5D, a schematic cross-sectional view of an insulin delivery microneedle according to an embodiment of the present invention, which has a base unit 10, a plurality of needle units 20, and an insulin reservoir 40, is shown. The needle unit 20 is a unit having a sharp tip that pierces through the skin, and is integrated with the base unit 10. The base unit 10 is a sheet-like unit that supports a plurality of needle units 20, has the mechanical strength that can support the needle units 20, and is flexible enough to be deformed along the skin. The reservoir 40 is located between the base unit 10 and the needle units 20, for example, by forming the base unit 10 in a concave shape. The insulin filled in the reservoir 40 is released from the surface of the needle units 20 to the outside through the base unit 10 and the needle units 20.

EXAMPLES

The present invention will be specifically described by the examples below. However, the present invention should not be construed as being limited thereto.

Example 1: Gel Preparation

A gel body of a gel having a columnar shape (diameter in dimethylsulfoxide (DMSO) as a reaction solvent is 1 mm) is produced by blending N-isopropylmethacrylamide (NIPMAAm) as a gelling agent (main chain), 4-(2-acrylamidoethylcarbamoyl)-3-fluorophenylboronic acid (AmECFPBA) as a phenylboronic acid-based monomer, N-hydroxyethylacrylamide (HEAAm) as a hydroxyl monomer, N,N'-methylenebis-(acrylamide) (MBAAm) as a cross-linking agent, and 2,2'-azobisisobutyronitrile as a polymerization initiator in a charged molar ratio of 62/27/11/5/0.1 (mol %), and carrying out radical polymerization. Next, the gel body is immersed at 4° C. for 24 hours in a pH 7.4 phosphate buffered aqueous solution (155 mM NaCl) containing FITC (fluorescein isothiocyanate)-modified (bovine-derived) insulin (hereinafter, simply referred to as FITC-modified insulin) at a concentration of 0.5 mg/1 mL to diffuse the FITC-modified insulin into the gel body.

The gel body is then removed from the phosphate buffer solution by soaking in a 0.01 M hydrochloric acid at 37° C. for one hour, thereby forming a thin hydrated shrinking layer on the surface of the gel body (the skin layer). A glucose-responsive gel was produced with the FITC-modified insulin encapsulated (loaded) in the gel body.

Then, in a phosphate buffered aqueous solution (155 mM NaCl) adjusted to pH 7.4, ionic strength 0.15, and a glucose concentration of 0.5 g/L, 1 g/L, 3 g/L, 5 g/L, and 10 g/L, respectively, this glucose-responsive gel was immersed, and the phosphate buffered aqueous solution of each glucose concentration was adjusted to a temperature of 25° C. to 45° C., respectively. Then, the degree of swelling $(d/do)^3$ of each glucose-responsive gel was measured at a predetermined temperature at each glucose concentration.

The results of examining the glucose responsiveness of the prepared gel are shown in FIG. 1. As a result, it was found that the gel containing HEAAm can significantly reduce the temperature dependence near the normal blood glucose level (1 g/L).

Example 2: Analysis of the Temperature Sensitivity of Gels

Fifteen types of samples a to o have various blending ratios (mol %) of N-isopropylmethacrylamide (NIP-MAAm), 4-(2-acrylamidoethylcarbamoyl)-3-fluorophenylboronic acid (AmECFPBA) and N-hydroxyethylacrylamide (HEAAm) were prepared by the same procedure as in Example 1. Here, the gel sample a was prepared by mixing N-isopropylmethacrylicamide (NIPMAAm) and 4-(2-acrylamidoethylcarbamoyl)-3-fluorophenylboronic acid (AmECFPBA) prepared at a blending ratio of 90:10 (mol %), and adding N-hydroxyethylacrylamide (HEAAm) to the mixture at a volume ratio of 90:10 (final molar ratio: 81/9/10). Similarly, the gel sample b was prepared by mixing N-isopropylmethacrylicamide (NIPMAAm) and 4-(2-acrylamidoethylcarbamoyl)-3-fluorophenylboronic acid (AmECFPBA) prepared at a blending ratio of 90:10 (mol %), and adding N-hydroxyethylacrylamide (HEAAm) to the mixture at a volume ratio of 80:20 (final molar ratio: 85/10/5). Other gel samples also contain these three components in the indicated proportions. The gel sample d is a conventional gel that does not contain HEAAm. The gel sample i is the gel shown in Example 1, and is the same as in the graph shown in FIG. 1.

Figure 2:
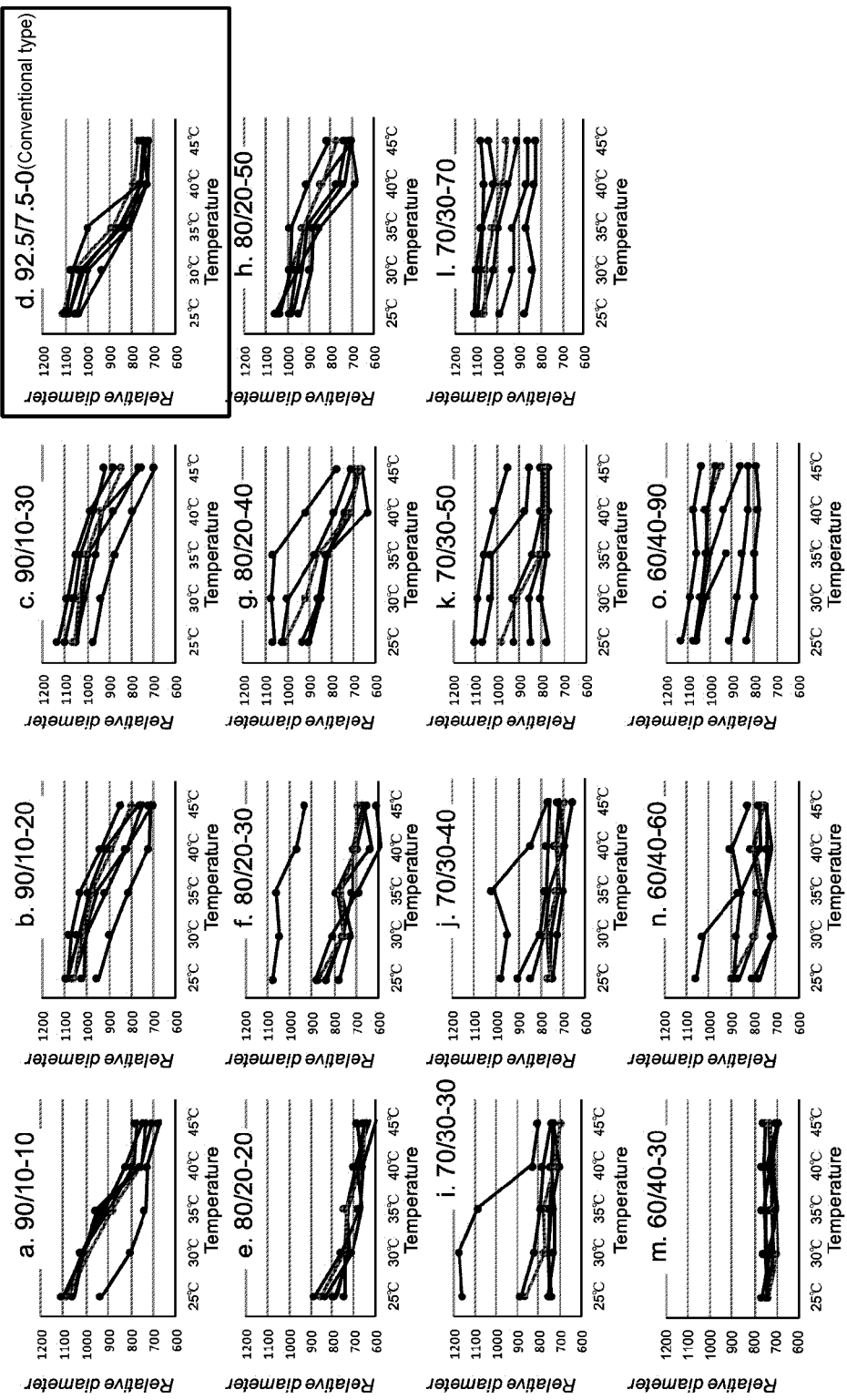
FIG. 2 is a graph showing the result of examining the glucose responsiveness of each of the prepared gels for fifteen types of samples a to o which have different blending ratios (mol %) of N-isopropylmethacrylamide (NIPMAAm), 4-(2-acrylamideethylcarbamoyl)-3-fluorophenylboronic acid (AmECFPBA) and N-hydroxyethylacrylamide (HEAAm). Here, the gel sample d is a conventional gel that does not contain HEAAm. The gel sample i is the gel shown in Example 1, and has the same graph as that shown in FIG. 1. The horizontal axis is temperature (Temperature), and the vertical axis is relative volume of the gels (Relative volume). The relative volume tends to increase in a concentration-dependent manner in response to the glucose concentrations of 0 g/L, 1 g/L, 2 g/L, 3 g/L, 5 g/L, and 10 g/L, respectively. It can be seen that the temperature sensitivity of the gel varies according to the change in the blending ratio of AmECFPBA and HEAAm in the composition.

The results of examining the glucose responsiveness of each of the prepared gels are shown in FIG. 2. It can be seen that the temperature sensitivity of the gel is changed by varying the blending ratio of AmECFPBA and HEAAm in the gel composition. Here, when the blending ratio (mol %) of AmECFPBA is small (NIPMAAm90:AmECFPBA10) as in the gel samples a to d, the change in temperature affects the volume of the gel regardless of the volume ratio of HEAAm. However, if the blending ratio (mol %) of AmECFPBA is increased as in the gel samples a, e, i, and m, even if the temperature changes, effect on the gel volume near the normal blood glucose level (1 g/L) is reduced (the top broken line for the gel sample i is 10 g/L as shown in FIG. 1). Therefore, the blending ratio of AmECFPBA to NIPMAAm is preferably 30 mol % or more. Further, as long as the blending ratio of AmECFPBA is 30 mol % or more, increasing the volume ratio of HEAAm as in the gel samples i to l can reduce the effect on the gel volume due to temperature change (including 10 g/L) regardless of glucose concentration. For example, the gel sample l is considered to be excellent in terms of temperature resistance, and there is almost no effect on the volume of the gel even if the temperature changes. Therefore, the volume ratio of HEAAm to the mixture of NIPMAAm and AmECFPBA is preferably 30 or more.

Example 4: Release Behavior of Temperature-Resistant Gels

One hollow fiber used in the polysulfone dialyzer (APS-15SA4537693003682) manufactured by Asahi Medeikaru Corp. was used as the device (internal diameter 185 µm, thickness 45 µm). In this example, a commercially available silicon catheter for insulin (4 Fr: inner diameter of about 600 µm, Prime Tech Co., Ltd.) was connected to the device to function as a reservoir for supplying insulin.

The insulin release experiment was performed using two pumps, and a high performance liquid chromatography (HPLC) system with an internal detector for refractive index (RI), UV and fluorescence intensity (JASCO, Japan).

By immersing the gel prepared in the same manner as in Example 1 in PBS containing 130 mg/L of the FITC-labeled bovine insulin (WAKO, Japan) at 4° C. for 24 hours, the FITC-labeled insulin was encapsulated in the gel. The gel was then filled into the device of the present invention and the device was quickly placed in a 0.01 M HCl aqueous solution and incubated at 37° C. for 60 minutes to form a skin layer on the gel surface.

The device of the present embodiment containing insulin and the gel was packed into a Tricorn Empty High-Performance Column of internal diameter 10 mm, length 50 mm (GE Healthcare, USA). The column was placed in PBS (pH 7.4, I=0.15) containing 1 g/L glucose at a constant temperature stream (25° C. to 45° C.), and connected to the HPLC system with the flow rate in the chamber maintained at 1 ml/min. Over 2-3 hours, an equilibrium state was obtained in which no leakage of insulin bound to the gel surface was observed.

The 520 nm fluorescence intensity (excitation wavelength: 495 nm) of the solution was monitored to measure the amount of the FITC-labeled insulin released from the gel. PBS containing and not containing 10 g/L glucose were prepared and supplied to the program from two pumps of the system. The solutions supplied from the pumps were continuously mixed by the mixer unit to have a predetermined glucose concentration gradient pattern (0 to 5 g/L). The in situ glucose concentration during the experiment was monitored by an RI detector in the downstream area near the column.

Figure 3:
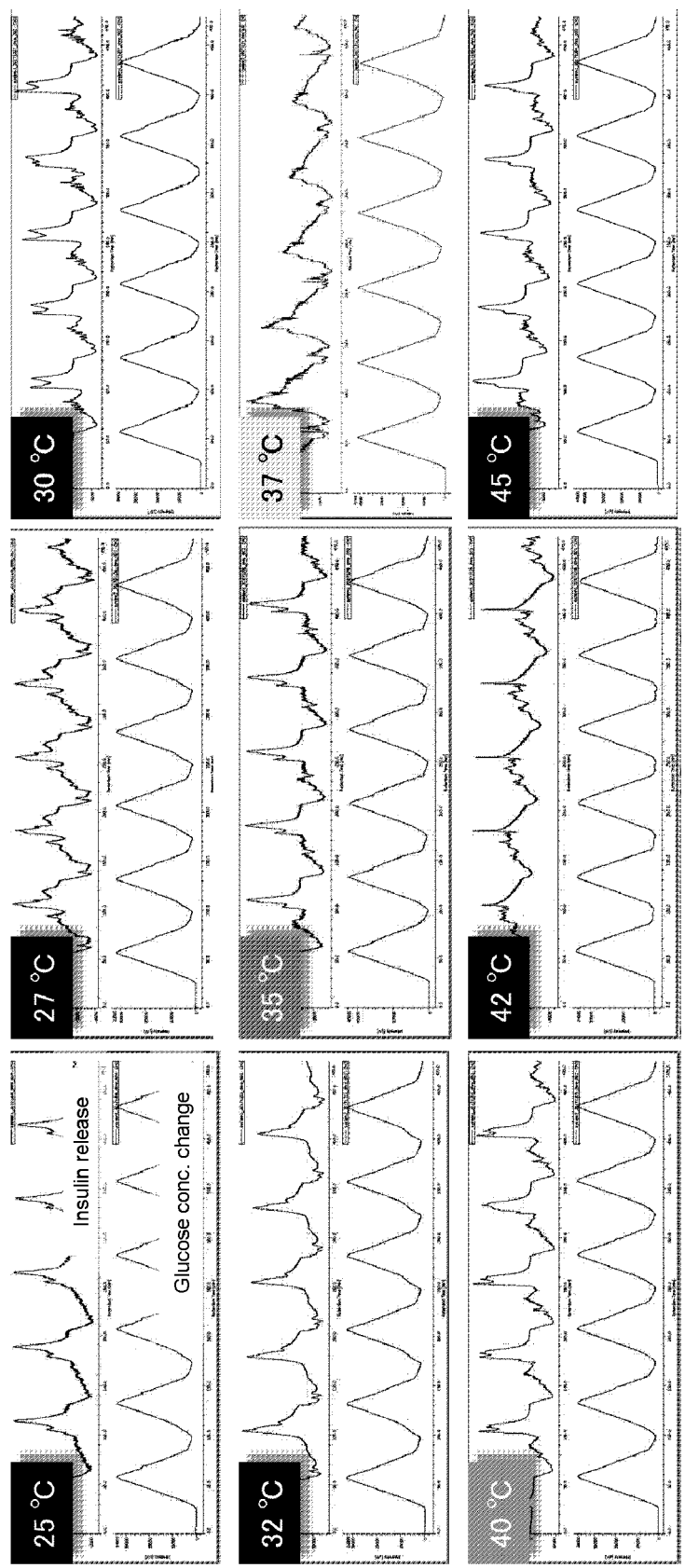
FIG. 3 is a graph showing the result of testing the release behavior of a temperature resistant gel containing N-hydroxyethylacrylamide (HEAAm). The test was performed at each temperature of 25° C. to 45° C. Insulin release in response to changes in the glucose concentration in the lower row is shown in the upper row. The horizontal axis is time and the vertical axis is concentration (fluorescence intensity). It can be seen that the tested gel can suppress temperature dependence and achieve a stable release behavior in the observation range of 25° C. to 45° C.

The results are shown in FIG. 3. As a result, it was found that the gel tested was capable of achieving a stable release behavior with reduced temperature dependence in the observation range of 25° C. to 45° C.

Example 5: Comparison of Old Gel and New Temperature-Resistant Gel

Figure 4A:
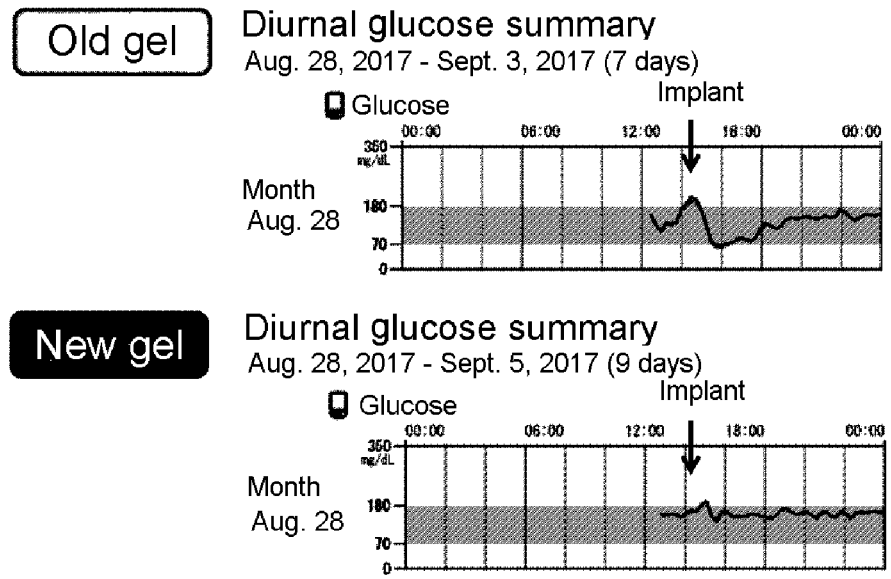
FIG. 4A shows a graph (continuous glucose measurement data) of investigating the suppression of hypothermia due to low body temperature at the time of device implantation in rats using an old gel (upper) and a new gel (lower). FreeStyle Libre Pro was used for the measurement. The vertical axis of the graph represents glucose concentration, and the horizontal axis represents time. In the new gel containing N-hydroxyethylacrylamide (HEAAm), improvement in temperature resistance, especially resistance to low temperature was observed. In addition, in the new gel, the amount of basal secretion has been optimized and suppression of the basal secretion amount has been achieved.
Figure 4B:
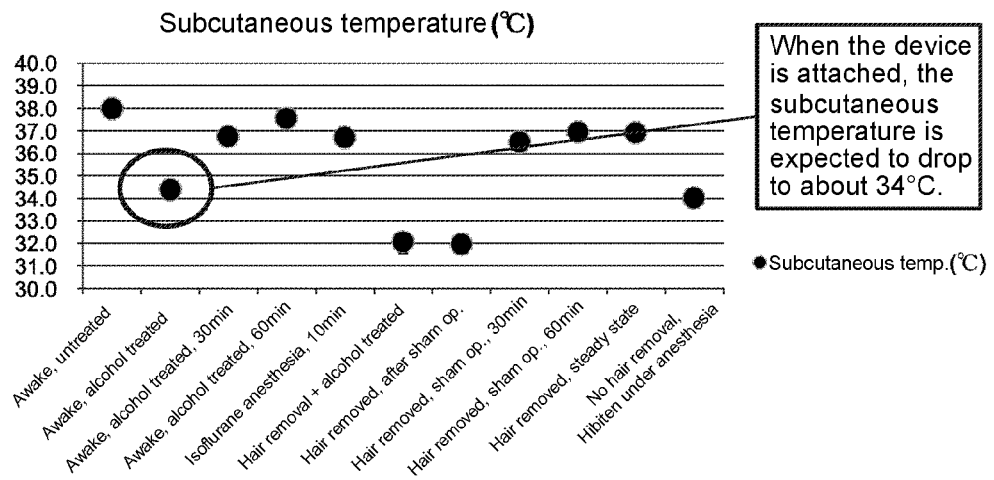
FIG. 4B is a graph showing the result of monitoring the subcutaneous temperature of rats using a microchip. The vertical axis represents the subcutaneous temperature. It was found that the subcutaneous temperature dropped significantly to about 34° C. by various operations and procedures such as alcohol disinfection and hair removal shown on the horizontal axis.
Figure 4C:
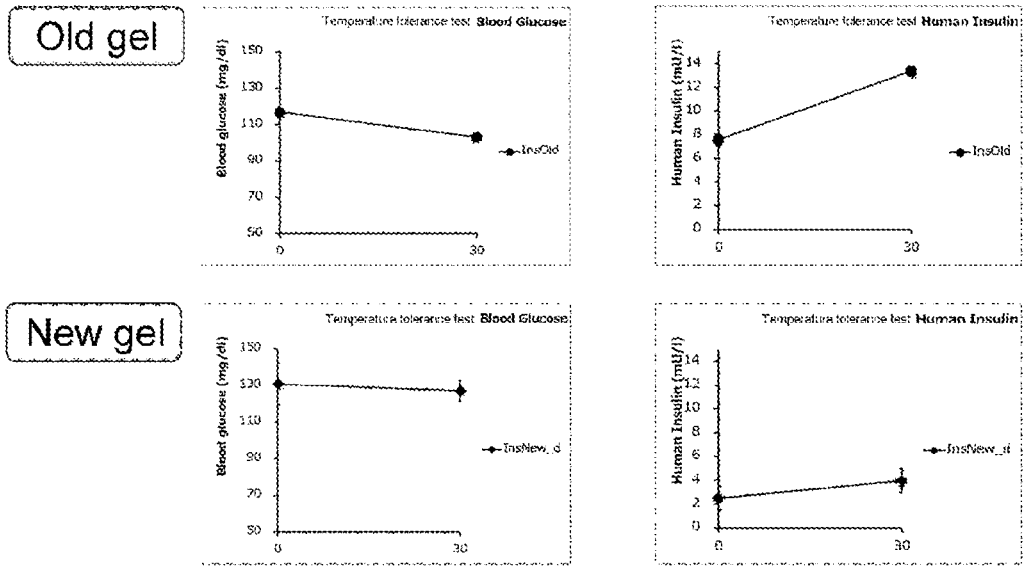
FIG. 4C is a graph showing comparison of the temperature resistance between a new gel according to an embodiment of the present invention and a conventional gel. In the temperature resistance experiment, a low temperature load was applied by spraying ethanol under anesthesia with isoflurane. The horizontal axis is time (minutes). The vertical axis is blood glucose concentration (Blood glucose; mg/dl; left) and human insulin concentration (Human insulin; mU/l; right), respectively. While insulin release and reduction of blood sugar were observed in the conventional-type gel with a low-temperature load, it was the new-type gel that showed a good temperature resistance at the low temperature load test.

An implantable device with a structure of dialysis hollow fibers coated with an old gel that does not contain HEAAm or a new gel containing HEAAm (PCT/JP2016/081407) was used to investigate the suppression of hypoglycemia due to low body temperature that occurs during rat implantation (data from a continuous glucose meter). FreeStyle Libre Pro was used for the measurement. FreeStyle Libre Pro is a self-monitoring blood glucose meter marketed by Abbott. The measurement result of the blood glucose level when the insulin delivery device was implanted in the rat is shown in FIG. 4A. When a device was placed on the left side of the back of the rat and a continuous blood glucose monitoring device was placed on the right side of the back to measure fluctuation of the blood glucose level after the implantation operation, it was revealed that the old gel caused hypoglycemia early after the operation (FIG. 4A). When the subcutaneous temperature of the rat was monitored using a microchip, it was found that the subcutaneous temperature was significantly reduced to about 34° C. by various operations and procedures such as alcohol disinfection and hair removal (FIG. 4B). On the other hand, in the new gel, the blood glucose level did not decrease immediately after implantation, and temperature resistance was improved, especially the resistance to low temperature. In addition, with the new gel, optimization of the amount of basal secretion was realized, and suppression of the amount of basal secretion was achieved.

The present specification shows the preferred embodiments of the present invention, and it is clear to those skilled in the art that such embodiments are provided simply for the purpose of exemplification. A skilled artisan may be able to make various transformations, and add modifications and substitutions without deviating from the present invention. It should be understood that the various alternative embodiments of invention described in the present specification may be used when practicing the present invention. Further, the contents described in all publications referred to in the present specification, including patents and patent application documents, should be construed as being incorporated the same as the contents clearly written in the present specification by their citation.

INDUSTRIAL APPLICABILITY

The present invention can provide glucose-responsive gels that are highly resistant to temperature changes. The present invention can also provide drug delivery devices using gels that are resistant to such temperature changes. Normally, the body temperature of mammals including humans is kept nearly constant. However, for example, at the start of a treatment with a drug delivery device, the patient's body temperature may drop temporarily after anesthetizing the patient or immediately after mounting the drug delivery device to the body. It is not desirable that the gel in the drug delivery device is affected by temperature changes to cause excessive drug delivery. For example, excessive delivery of insulin causes hypoglycemia. The glucose-responsive gels developed by the present inventors have high resistance to temperature changes and can reduce the risk of unwanted excessive drug release when the drug delivery device is attached. Therefore, it can be said that they are more useful and safer than the conventional glucose-responsive gels.

DESCRIPTION OF NUMERICAL SYMBOLS

1 insulin delivery device, 2 catheter, 3 reservoir, 4 catheter side wall, 5 side hole, 6 gel filling unit, 7 insulin solution filling unit, 10 base unit, 20 needle unit, 30 sheet, 40 reservoir, 50 adhesive

The invention claimed is:

1. A glucose-responsive gel formed by copolymerization of a gel composition comprising 4-(2-acrylamidoethylcarbamoyl)-3-fluorophenylboronic acid (AmECFPBA), N-hydroxyethylacrylamide (HEAAm), and N-isopropylmethacrylamide (NIPMAAm), wherein a blending ratio of AmECFPBA to NIPMAAm is 30 mol % or more.

2. The glucose-responsive gel according to claim 1, wherein a volume ratio of HEAAm to the mixture of NIPMAAm and AmECFPBA is 30% or more.

3. The glucose-responsive gel according to claim 1, further comprising a cross-linking agent in the gel composition.

4. The glucose-responsive gel according to claim 3, wherein the crosslinking agent is N,N'-methylenebis-(acrylamide) (MBAAm).

5. The glucose-responsive gel according to claim 1, wherein the gel composition comprises 5 mol % to 40 mol % of 4-(2-acrylamidoethylcarbamoyl)-3-fluorophenylboronic acid (AmECFPBA), 10 mol % to 70 mol % of N-hydroxyethylacrylamide (HEAAm), and 20 mol % to 80 mol % of N-isopropylmethacrylamide (NIPMAAm).

6. A drug delivery device comprising the glucose-responsive gel according to claim 1.

7. The drug delivery device according to claim 6, which is an implantable-type or microneedle-type device.

8. The drug delivery device according to claim 6, which is a device for use in insulin delivery.

9. A glucose-responsive gel comprising a copolymer of monomers comprising 4-(2-acrylamidoethylcarbamoyl)-3-fluorophenylboronic acid (AmECFPBA), N-hydroxyethylacrylamide (HEAAm), and N-isopropylmethacrylamide (NIPMAAm), wherein a blending ratio of AmECFPBA to NIPMAAm is 30 mol % or more.

10. The glucose-responsive gel according to claim 9, wherein a volume ratio of HEAAm to the mixture of NIPMAAm and AmECFPBA is 30% or more.

* * * * *